(12) United States Patent
Shin et al.

(10) Patent No.: US 8,101,716 B2
(45) Date of Patent: Jan. 24, 2012

(54) HUMAN INTERFERON-BETA MUTEIN

(75) Inventors: Young Kee Shin, Seoul (KR); Moon Kyoung So, Suwon-si (KR); Jong Min Lee, Seoul (KR); Ji-Hye Yang, Seoul (KR); Ji Uk Yoo, Daejeon (KR); Tae Ho Byun, Yongin-si (KR); Ji Tai Kim, Ansan-si (KR); Han Kyu Oh, Yongin-si (KR); Ho CHul Yoon, Suwon-si (KR); Ji Soo Ahn, Suwon-si (KR); Kyung Song, Incheon (KR); Jae Ho Jin, Goyang-si (KR)

(73) Assignee: Young Kee Shin, Seoul (KR)

( * ) Notice: Subject to any disclaimer, the term of this patent is extended or adjusted under 35 U.S.C. 154(b) by 758 days.

(21) Appl. No.: 11/718,449

(22) PCT Filed: Nov. 2, 2005

(86) PCT No.: PCT/KR2005/003665
§ 371 (c)(1),
(2), (4) Date: May 31, 2007

(87) PCT Pub. No.: WO2006/049423
PCT Pub. Date: May 11, 2006

(65) Prior Publication Data
US 2010/0003721 A1  Jan. 7, 2010

(30) Foreign Application Priority Data

Nov. 2, 2004  (KR) .................. 10-2004-0088196

(51) Int. Cl.
| | |
|---|---|
| *C07K 14/00* | (2006.01) |
| *C07K 14/52* | (2006.01) |
| *C12N 15/00* | (2006.01) |
| *C12P 21/04* | (2006.01) |
| *A61K 38/21* | (2006.01) |

(52) U.S. Cl. .... 530/351; 530/350; 435/69.1; 435/69.51; 435/69.7; 435/70.1; 435/320.1; 424/85.1; 424/85.6

(58) Field of Classification Search ........................ None
See application file for complete search history.

(56) References Cited

U.S. PATENT DOCUMENTS

2004/0137581 A1* 7/2004 Aguinaldo et al. ........ 435/69.52

OTHER PUBLICATIONS

Ngo et al., 1994, The Protein Folding Problem and Tertiary Structure Prediction, pp. 492-495.*
Wells, Aditivity of Mutational Effects in Proteins, 1990, Biochemistry, vol. 26, No. 37, pp. 8509-8517.*

* cited by examiner

*Primary Examiner* — Christine J Saoud
*Assistant Examiner* — Jegatheesan Seharaseyon
(74) *Attorney, Agent, or Firm* — Lucas & Mercanti, LLP

(57) ABSTRACT

The present invention relates to a human interferon-beta mutein. In particular, the present invention relates to the human interferon-beta mutein having one or two additional sugar chains compared to natural human interferon-beta.

13 Claims, 10 Drawing Sheets

FIG. 1.

```
1   atg acc aac aag tgt ctc ctc caa att gct ctc ctg ttg tgc ttc tcc act aca gct ctt
    M   T   N   K   C   L   L   Q   I   A   L   L   L   C   F   S   T   T   A   L
                1
61  tcc atg agc tac aac ttg ctt gga ttc cta caa aga agc agc aat ttt cag tgt cag aag
    S   M   S   Y   N   L   L   G   F   L   Q   R   S   S   N   F   Q   C   Q   K
              20                        27
121 ctc ctg tgg caa ttg aat ggg agg ctt gaa tat tgc ctc aag gac agg atg aac ttt gac
    L   L   W   Q   L   N   G   R   L   E   Y   C   L   K   D   R   M   N   F   D
                                    ↓
                                   T/S
          40
181 atc cct gag gag att aag cag ctg cag cag ttc cag aag gag gac gcc gca ttg acc atc
    I   P   E   E   I   K   Q   L   Q   Q   F   Q   K   E   D   A   A   L   T   I
          60
241 tat gag atg ctc cag aac atc ttt gct att ttc aga caa gat tca tct agc act ggc tgg
    Y   E   M   L   Q   N   I   F   A   I   F   R   Q   D   S   S   S   T   G   W
          80
301 aat gag act att gtt gag aac ctc ctg gct aat gtc tat cat cag ata aac cat ctg aag
    N   E   T   I   V   E   N   L   L   A   N   V   Y   H   Q   I   N   H   L   K
          100
361 aca gtc ctg gaa gaa aaa ctg gag aaa gaa gat ttt acc agg gga aaa ctc atg agc agt
    T   V   L   E   E   K   L   E   K   E   D   F   T   R   G   K   L   M   S   S
          120
421 ctg cac ctg aaa aga tat tat ggg agg att ctg cat tac ctg aag gcc aag gag tac agt
    L   H   L   K   R   Y   Y   G   R   I   L   H   Y   L   K   A   K   E   Y   S
          140
481 cac tgt gcc tgg acc ata gtc aga gtg gaa atc cta agg aac ttt tac ttc att aac aga
    H   C   A   W   T   I   V   R   V   E   I   L   R   N   F   Y   F   I   N   R
          160
541 ctt aca ggt tac ctc cga aac tga aga tct cct agc ctg tcc ctc tgg gac tgg aca att
    L   T   G   Y   L   R   N   Stop
                                    ggtaatatcactgtc
                                     G  N  I  T  V
```

HUMAN INTERFERON-BETA MUTEIN

CROSS-REFERENCE TO RELATED APPLICATION

This application is a 371 of PCT/KR2005/003665 filed on Nov. 2, 2005, which claims the benefit of Korean Patent Application No. 10-2004-0088196 filed on Nov. 2, 2004, the contents of each of which are incorporated herein by reference.

FIELD OF THE INVENTION

The present invention relates to a human interferon-beta mutein. In particular, the present invention relates to the human interferon-beta mutein having one or two additional sugar chains compared to natural human interferon-beta.

BACKGROUND OF THE INVENTION

Interferon (IFN) which is a member of cytokines shows antiviral activity, suppresses cell proliferation and regulates natural immune response. Interferon-beta (IFN-β) is a spherical protein having 5 helices and has a molecular weight of 22 kDa which becomes 18 kDa when removed its sugar chain (Arduini et al., *Protein Science* 8: pp 1867-1877, 1999).

Interferon-beta has been actively studied for its clinical applications, and in particular, it has been in the spotlight as a relieving, alleviating or treating agent for multiple sclerosis symptom (Goodkin et al., Multiple sclerosis: Treatment options for patients with relapsing-remitting and secondary progressive multiple sclerosis, 1999).

Besides multiple sclerosis, it has been reported that interferon-beta shows diverse immunological activities such as antiviral activity, cell growth inhibition or anti-growth activity, increasing lymphocytotoxicity, immunoregulatory activity, inducing or suppressing proliferation of target cells, activating macrophages, increasing cytokine production, increasing cytotoxicity T cell effect, increasing natural killer cells, and therefore, it is effectively used for treating cancer, auto-immune disorders, viral infections, HIV-relating diseases, hepatitis C, rheumatoid arthritis and the like (Pilling et al., *European Journal of Immunology* 29: pp 1041-1050, 1999, Young et al., *Neurology* 51: pp 682-689, 1998; Cirelli et al., Major therapeutic uses of interferons. *Clin Immunother* 3: pp 27-87, 1995).

Human interferon-beta is a kind of glycoproteins linked to one or more sugar chains, and such sugar chain plays an important role in the glycoprotein's activity.

Therefore, there is an instance where a glycoprotein's activity becomes increased when a sugar chain is additionally introduced thereto.

PCT Publication No. WO96/25498 and U.S. Pat. No. 5,618,698 have disclosed that the activities of hTPO and hEPO glycoproteins are increased by introducing with one or more sugar chains.

The present invention has disclosed a human interferon-beta mutein having increased or improved activity or ability by introducing with a sugar chain into human natural interferon-beta, as a point of view described above.

Accordingly, in an embodiment of the present invention, there is provided a human interferon-beta mutein having increased or improved activity or ability by introducing a sugar chain into human natural interferon-beta.

Other objects or embodiments according to the present invention are provided hereunder.

DETAILED DESCRIPTION OF THE INVENTION

In a preferred embodiment, the present invention relates to a human interferon-beta mutein.

Since the human interferon-beta mutein of the present invention takes the form of introducing with one or two additional sugar chains to natural human interferon-beta, it shows improved or increased antiviral activity, cell growth suppression activity, immunoregulatory ability and prolonged in vivo half-life (see FIGS. 7 to 10).

As described in the following Examples, in case of expressing the polypeptide being replaced the $27^{th}$ amino acid, arginine (R) in the natural human interferon-beta having the amino acid sequence of SEQ ID NO: 1 with threonine (T) or serine (S) or being added with a glycine-asparagine-isoleucine-valine (G-N-I-T-V) sequence to the C-terminal end of the natural human interferon-beta in an animal cell, the present invention can prepare a human interferon-beta mutein having improved or increased activity or ability compared to the natural human interferon-beta by introducing with one or two additional N-linked sugar chains into the natural interferon-beta.

The present invention is provided based on these experimental results.

The human interferon-beta mutein having increased or improved activity or ability compared to the natural human interferon-beta is characterized by including the glycine-asparagine-isoleucine-valine (G-N-I-T-V) sequence at the C-terminal end in the amino acid sequence of the natural human interferon-beta or a natural human interferon-beta mutein and having a N-linked sugar chain at that sequence position.

The term "natural human interferon-beta mutein" used herein including claims means all polypeptides harboring a part of or the whole amino acid sequence derived from the natural human interferon-beta with maintaining human interferon-beta activity.

The term "human interferon-beta activity" used herein means one or more activities sufficient to define a polypeptide as human interferon-beta among the previously known activities being exhibited by human interferon-beta. Such activities include activity for relieving, alleviating or treating multiple sclerosis, antiviral activity, cell growth inhibition, anti-growth activity, anti-proliferation, increasing lymphocytotoxicity, immunoregulatory activity, inducing or suppressing target cell's proliferation, increasing cytokine production, increasing cytotoxic T cell effect, increasing natural killer cell, activity for preventing or treating cancer, preventing or treating auto-immune disorders, preventing or treating viral infections, preventing or treating HIV-relating diseases, preventing or treating hepatitis C and preventing or treating rheumatoid arthritis.

Further, the term "polypeptide harboring a part of or the whole amino acid sequence derived from the natural human interferon-beta" used herein means a polypeptide containing the whole amino acid sequence of the natural human interferon-beta represented by SEQ ID NO: 1 or an essential part thereof, or a polypeptide substantially similar to such polypeptide.

The term "polypeptide including an essential part of the whole amino acid of SEQ ID NO: 1" used herein means a polypeptide which shows relatively lower activity than the natural human interferon-beta having the amino acid sequence of SEQ ID NO: 1, but contains a part of the amino acid sequence of SEQ ID NO: 1 with still harboring the human interferon-beta activity. In addition, the term "polypeptide substantially similar to the whole amino acid sequence of SEQ ID NO: 1 or an essential part thereof" used herein means a polypeptide which shows relatively lower activity than the natural human interferon-beta having the amino acid sequence of SEQ ID NO: 1, but contains the whole amino acid sequence of SEQ ID NO: 1 or an essential part thereof having one or more substituted amino acids with still harboring the human interferon-beta activity.

For example, the polypeptide including an essential part of the whole amino acid sequence of SEQ ID NO: 1 may be a polypeptide being deleted its N-terminal and/or C-terminal end in the polypeptide having the amino acid sequence of SEQ ID NO: 1. Further, the polypeptide substantially similar to the whole amino acid sequence of SEQ ID NO: 1 or an essential part thereof is exemplified by a polypeptide having one or more substituted amino acids wherein the substituted amino acid is chemically equivalent to the original amino acid before the substitution. For example, in case of a hydrophobic amino acid such as alanine, it is preferable to replace with another hydrophobic amino acid such as glycine or further hydrophilic amino acid such as valine, leucine or isoleucine than the original amino acid.

Sometimes, since the N-terminal end, the C-terminal end or the substituted amino acid may influence on a motif essential for the activity of human interferon-beta, there are instances where the polypeptide being deleted its N-terminal end and/or C-terminal end or having a substituted amino acid does not show any human interferon-beta activity. Nevertheless, by confirming whether a polypeptide derived from the amino acid sequence of SEQ ID NO: 1 has one or more activities among the activities described above, and/or through a well-known method in the art relating to the identification of human interferon-beta based on the time for a filing date of the present invention, to classify and detect an active polypeptide from such inactive polypeptides belongs to a conventional capacity range of a skilled person in the art.

The above description being collectively considered, the human interferon-beta mutein of the present invention may be defined as one of the following polypeptides which contain a glycine-asparagine-isoleucine-threonine sequence at its C-terminal end, have an N-linked sugar chain at that sequence position and show the human interferon-beta activity:

(a) a polypeptide containing the whole amino acid sequence of SEQ ID NO: 1;

(b) a polypeptide including an essential part of the amino acid sequence of SEQ ID NO: 1; and (c) a polypeptide substantially similar to the polypeptide (a) or (b).

Therefore, it has to be understood that the human interferon-beta mutein of the present invention is a polypeptide harboring the human interferon-beta activity which contains a glycine-asparagine-isoleucine-threonine sequence at its C-terminal end and has an N-linked sugar chain at that sequence position.

Likewise, although the human interferon-beta mutein of the present invention is defined and understood as all polypeptides showing the human interferon-beta activity which contain a glycine-asparagine-isoleucine-threonine sequence at their C-terminal ends and have an N-linked sugar chain at that sequence position, the preferred human interferon-beta mutein of the present invention is a polypeptide which contains a glycine-asparagine-isoleucine-threonine sequence at the C-terminal end of the natural human interferon-beta having the amino acid sequence of SEQ ID NO: 1 and has an N-linked sugar chain at that sequence position.

Further, the preferred human interferon-beta mutein of the present invention is a polypeptide substantially similar to the polypeptide containing the whole amino acid sequence of SEQ ID NO: 1 or an essential part thereof (corresponding to the above polypeptide (C)). Such polypeptide contains two N-linked sugar chains: one is located at the glycine-asparagine-isoleucine-threonine sequence of its C-terminal end, and the other is located at the $25^{th}$ to the $28^{th}$ amino acid sequences of SEQ ID NO: 1 consisting of asparagine-glycine-theronine/serine-leucine, which is modified by replacing the $27^{th}$ amino acid arginine of SEQ ID NO: 1 with threonine or serine.

The most preferred form in the human interferon-beta muteins of the present invention is a polypeptide which contains a N-linked sugar chain at the position where the $27^{th}$ amino acid arginine of SEQ ID NO: 1 is replaced with threonine or serine, and contains another N-linked sugar chain at the position where the glycine-asparagine-isoleucine-threonine sequence is added to its C-terminal end.

The following Examples of the present invention show that the human interferon-beta mutein introduced with two additional sugar chains exhibits further improved or increased activity or ability than the human interferon-beta mutein introduced with only one additional sugar chain compared to the natural human interferon-beta (see Examples 5 and 6, and FIGS. 7 to 10).

Meanwhile, the human interferon-beta mutein of the present invention may be defined with a different way as the following.

In particular, the human interferon-beta mutein of the present invention can be defined as a polypeptide showing the human interferon-beta activity as one of the following polypeptides which is introduced with an additional N-linked sugar chain into the position where the $25^{th}$ to the $28^{th}$ amino acid sequences of SEQ ID NO: 2 consisting of asparagine-glycine-threonine/serine-leucine are conserved:

(a) a polypeptide containing the whole amino acid sequence of SEQ ID NO: 2;

(b) a polypeptide including an essential part of the amino acid sequence of SEQ ID NO: 2; and (c) a polypeptide substantially similar to the polypeptide (a) or (b).

The paragraph "the $25^{th}$ to the $28^{th}$ amino acid sequences consisting of asparagine-glycine-theronine/serine-leucine are conserved" used herein including claims means that the $25^{th}$ to the $28^{th}$ amino acid sequences consisting of asparagine-glycine-theronine/serine-leucine must be present at the polypeptide (b) or (c) (i.e., the polypeptide including an essential part of the amino acid sequence of SEQ ID NO: 2 or the polypeptide substantially similar to the whole or an essential part of the amino acid sequence of SEQ ID NO: 2).

When the human interferon-beta mutein of the present invention is defined with a different way as described above, the preferred human interferon-beta mutein of the present invention is a polypeptide containing the whole amino acid sequence of SEQ ID NO: 2 which is introduced with an additional N-linked sugar chain into the position of the $25^{th}$ to the $28^{th}$ amino acid sequences consisting of asparagine-glycine-theronine/serine-leucine.

The amino acid sequence of SEQ ID NO: 2 is the sequence being replaced the $27^{th}$ amino acid arginine in the amino acid sequence of SEQ ID NO: 1 with threonine or serine.

Meanwhile, the term "polypeptide including an essential part of the amino acid sequence of SEQ ID NO: 2" or "polypeptide substantially similar to the whole or an essential part of the amino acid sequence of SEQ ID NO: 2" has the same meaning as described above.

In another embodiment, the present invention relates to a polynucleotide encoding the human interferon-beta mutein as described above.

The term "human interferon-beta mutein as described above" includes the human interferon-beta muteins of the present invention as defined above with two different ways and all the preferred embodiments each thereof.

When given a certain amino acid sequence, a skilled person in the art can easily synthesize a polynucleotide encoding the certain amino acid sequence based on the given sequence by employing his conventional techniques.

The term "polynucleotide" used herein is defined as the meaning including all single-strand or double-strand RNA or DNA or a polymer thereof.

Meanwhile, when considered the activity, the above polynucleotide is preferable to be a polypeptide encoding the human interferon-beta mutein which is introduced with a glycine-asparagine-isoleucine-threonine-valine sequence into the C-terminal end of the natural human interferon-beta consisting of the amino acid sequence of SEQ ID NO: 1 or a polynucleotide encoding the human interferon-beta mutein consisting of the amino acid sequence of SEQ ID NO: 2. More preferably, the polynucleotide is a polynucleotide encoding the human interferon-beta mutein which is introduced with the glycine-asparagine-isoleucine-thereonine-valine sequence into the C-terminal end of the natural human interferon-beta consisting of the amino acid sequence of SEQ ID NO: 1 and has the substitution of the $27^{th}$ amino acid arginine with threonine or serine.

In another embodiment, the present invention relates to an animal cell expression vector comprising the polynucleotide described above which is capable of expressing the human interferon-beta mutein of the present invention in the animal cell.

The human interferon-beta mutein of the present invention includes one or two additional sugar chains compared to the natural human interferon-beta. When considered the fact that the addition of such sugar chain is a phenomenon generally occurred in an animal cell, the animal cell expression vector fundamentally comprises:

(i) the polynucleotide encoding the human interferon-beta mutein as described above;
(ii) a promoter operably linked to the nucleotide sequence of (i) which generates a RNA molecule;
(iii) a polynucleotide encoding a leader sequence;
(iv) a replication origin; and
(iv) 3'-untranslated region (3'-UTR) causing polyadenylation of the 3'-terminal end of the RNA molecule.

The promoter employable in the present invention means the sequence capable of activating transcription, which is well-known in the art. Similarly, the leader sequence which leads to the translocation of a translated protein into the endoplasmic reticulum where a glycosylation is occurred and 3'-UTR capable of stabilizing the leader sequence and mRNA are well-known in the art.

Meanwhile, the expression vector of the present invention may selectively comprise a reporter gene (e.g., luciferase and β-glucuronidase) or an antibiotic resistance gene as a selective marker (e.g., neomycin, carbenicillin, kanamycin, spectinomycin, hygromycine), and may further comprise an enhancer.

Meanwhile, the animal cell expression vector employable in the present invention includes pSV2-neo (Southern and Berg, *J. Mol. Appl. Genet.* 1: 327-341, 1982), pCAGGS (Niwa et al., *Gene* 108: 193-200, 1991), pcDL-SRα296 (Takebe et al., *Mol. Cell. Biol.* 8: 466-472, 1988), pAc373 (Luckow et al., *Bio/Technology* 6: 47-55, 1988), and such vectors listed above may comprise a promoter, leader sequence, replication origin, 3'-UTR, reporter gene, selective marker gene and/or enhancer described above on occasion demands.

In another embodiment, the present invention relates to an animal cell transformed with the expression vector and a method for the production of a human interferon-beta mutein by culturing the animal cell.

The term "transformation" used herein including claims means the modification of a host cell's genotype by introducing with a foreign polynucleotide (in the present invention, which means a polynucleotide encoding the human interferon-beta mutein), and means the introduction of a foreign polynucleotide into a host cell regardless of the transformation method used. The foreign polynucleotide introduced into a host cell may be maintained with or without the integration into the host cell's genome, and the present invention includes the both cases.

Meanwhile, the term "animal cell" used herein includes all animal cells and insect cells employable in the production of a recombinant protein. Exemplary animal cells employable in the present invention include COS cells, CHO cells, C-127 cells, BHK cells, rat Hep I cells, rat Hep II cells, TCMK cells human pneumocytes, human hepatoma cells, HepG2 cells, mouse hepatocytes, DUKX cells, 293 cells and so on, and the insect cell is exemplified by a silkworm culture cell.

In another embodiment, the present invention relates to a pharmaceutical composition comprising the human interferon-beta mutein according to the present invention.

Human interferon-beta included in the pharmaceutical composition of the present invention has been generally used as a therapeutic agent for multiple sclerosis, but it has been also reported that it can be used for treating cancer, autoimmune disorders, viral infections, HIV-relating diseases and hepatitis C (Pilling et al., *European Journal of Immunology* 29: 1041-1050, 1999) and its new pharmacological effect has been continuously discovered.

Therefore, the pharmacological effect in the pharmaceutical composition of the present invention must be understood to include all the other pharmacological effects being exhibited by human interferon-beta as well as the pharmacological effect as a therapeutic agent for multiple sclerosis.

Further, such pharmacological effect must be understood to include any pharmacological effect that will be discovered in the future as well as all the pharmacological effects reported up to now as the pharmacological effect of human interferon-beta.

Since the pharmaceutical composition of the present invention is characterized by comprising the human interferon-beta mutein having improved or increased activity or ability prepared according to the method of the present invention, although the pharmaceutical composition of the present invention may include any pharmacological effect of human interferon-beta that will be discovered in the future as well as its all pharmacological effects reported up to now, the scope of the present invention is not to be unduly enlarged.

Nevertheless, when considered the fact that human interferon-beta has been widely used as a therapeutic agent for multiple sclerosis and its therapeutic effects for cancer, autoimmune disorders, viral infections, HIV-relating diseases and hepatitis C have been previously discovered, the above pharmacological effect is preferable to be such pharmacological effects.

Meanwhile, the pharmaceutical composition of the present invention can be administered via various routes including oral, transdermal, subcutaneous, intravenous and intramuscular introduction.

The inventive pharmaceutical composition may be formulated into several kinds of formulations in accordance with any of the conventional procedures. In preparing the formulation, the active ingredient is preferably admixed or diluted with diluents such as fillers, expanders, binders, wetting agent, disintegrants and surfactants or excipients.

For treating a human patient, a typical daily dose of the inventive pharmaceutical composition may range from about 0.01 to 5 µg/kg body weight, and can be administered in a single dose or in divided doses. However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

BRIEF DESCRIPTION OF THE DRAWINGS

FIG. 1 is the nucleotide sequence of a gene encoding human interferon-beta and the amino acid sequence encoded therein. The amino acid sequence being artificially substituted is represented as a box.

The following Examples are intended to further illustrate the present invention and they should not be construed as limiting the scope of the present invention.

Example 1

Synthesis of a Gene Encoding a Human Interferon-Beta Mutein Having One or More Additional Asn-X-Ser/Thr Sequences Via Mutagenesis In order to artificially modify R27 (the 27$^{th}$ amino acid sequence, arginine) in the amino acid sequence of human interferon-beta (IFN-β) presented by SEQ ID NO: 1 (FIG. 1) into threeonine (T) or serine (S), or to add a glycine-aspar-agine-isoleucine-threonine-valine sequence (G-N-I-T-V) to the C-terminal end of IFN-β, site-directed mutagenesis and DNA synthesis were conducted by using a gene encoding natural interferon-beta of SEQ ID NO: 3 as a template.

Namely, a series of primer pairs were synthesized by targeting for the site to be subjected to mutagenesis. At this time, the primer pairs used in overlapping PCR for synthesizing a gene encoding an interferon-beta mutein were as follows:

i) a primer pair for synthesizing R27T

```
R27T-5':
GCAATTGAATGGGACGCTTGAATACTGCCTC    (SEQ ID NO: 4)

R27T-3':
GAGGCAGTATTCAAGCGTCCCATTCAATTGC    (SEQ ID NO: 5)
``` ii) a primer pair for synthesizing R27S

```
R27S-5':
GCAATTGAATGGGAGTCTTGAATACTGCCTC    (SEQ ID NO: 6)

R27S-3':
GAGGCAGTATTCAAGACTCCCATTCAATTGC    (SEQ ID NO: 7)
``` iii) a primer pair for synthesizing GNITV

```
GNITV-5':
                                   (SEQ ID NO: 8)
CTTACAGGTTACCTCCGAAACGGTAATATCACTGTCTGAAGATCTCCTAG
CCTGTCC

GNITV-3':
                                   (SEQ ID NO: 9)
GAATGTCCAATGGAGGCTTTGCCATTATAGTGACAGACTTCTAGAGGATC
GGACAGG
```

(wherein R27T and R27S are the genes encoding interferon-beta muteins having the substitution of arginine at the 27$^{th}$ position with theronine and serine, respectively, through the mutagenesis of an interferon-beta gene, and GNITV is the gene encoding the interferon-beta mutein which is added a glycine-asparagine-isoleucine-threonine-valine (G-N-I-T-V) sequence to its C-terminal end through the mutagenesis of an interferon-beta gene. The followings are the same.)

Figure 2:
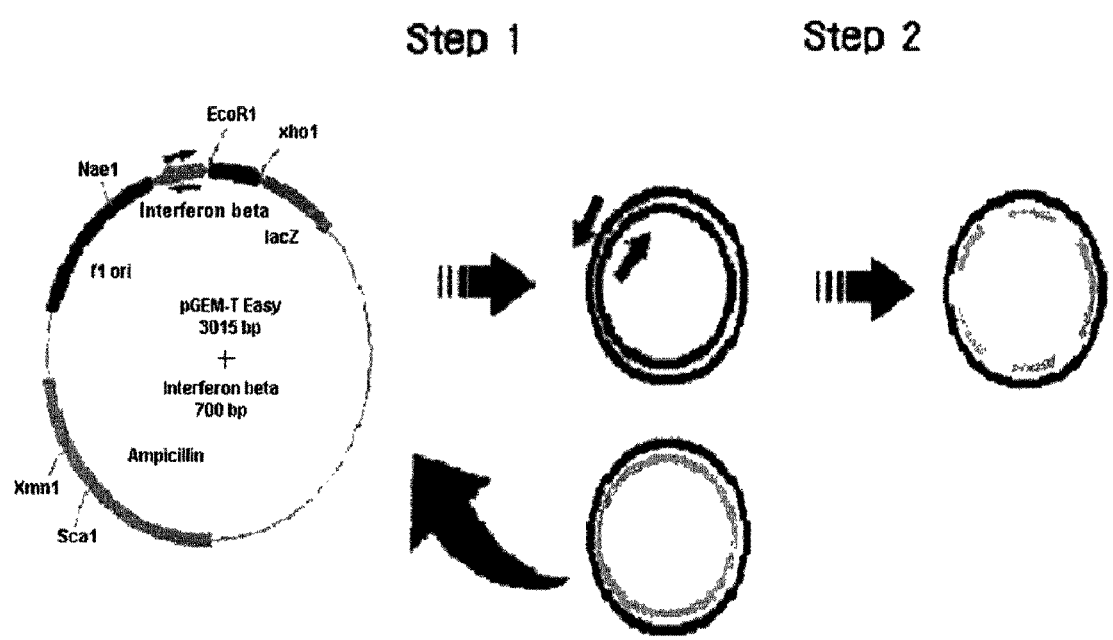
FIG. 2 is a scheme showing the procedure of artificially modifying the gene encoding human interferon-beta at a specific site by site-directed mutagenesis. In the first step, the synthesized primer pair binds to the specific site of the nucleotide sequence and synthesizes a new gene having the substituted nucleotide sequence by the action of DNA polymerase. In the second step, the methylated interferon-beta template gene within the PCR reaction mixture containing the newly synthesized interferon-beta gene is removed by treating with restriction enzyme DpnI, and the resulting PCR reaction mixture is transformed into *E. coli*.

As shown in FIG. 2, PCR was conducted by using plasmid pGEM-T Easy vector (Promega, USA) containing the gene encoding interferon-beta as a template, two overlapping primer pairs and Pfu-turbo DNA polymerase. PCR reaction solution was prepared by mixing 5 µl of a 10× reaction buffer solution, 5 to 50 ng of a template gene, 125 ng each of the primer pair and 1 µl of a dNTP mixture, its final volume was adjusted to 50 µl with ultrapure water, and then, 1 µl of Pfu Turbo DNA polymerase (2.5 U/µl) was added thereto. The PCR conditions were as follows: 12 cycles of 30 sec at 95° C., 60 sec at 55° C. and 480 sec at 68° C. after an initial denaturation of 30 sec at 95° C.

The PCR product was treated with 1 μl of DpnI (10 U/μl) at 37° C. for 4 hrs to remove the methylated template gene. After 1 μl of the DpnI treated PCR product was added to XL1-blue E. coli cells melted on ice, the mixture was heated at 42° C. for 45 sec and cooled by ice. E. coli cells thus prepared were suspended in 500 μl of a culture medium, incubated at 37° C. for an hour, and subjected to centrifugation to harvest the cells. Thus harvested cells were spread onto a LB agar plate, incubated at 37° C. for 16 hrs or more until a colony was generated. After plasmid DNA was purified from the colony, the gene encoding an interferon-beta mutein was subjected to sequencing analysis by using a DNA sequencer. As a result, the $27^{th}$ amino acid was modified into the codon encoding threonine (R27T) or serine (R27S) via site-directed mutagenesis. Further, the codon encoding the amino acid sequence (GNITV) consisting of glycine-asparagine-isoleucine-threonine-valine was added to the C-terminal end of the natural human interferon-beta. Plasmids containing thus prepared gene were designated pGEMT-IFN-β-R27T, pGEMT-IFN-β-R27S and pGEMT-IFN-β-GNITV, respectively.

PCR was performed by using pGEMT-IFN-β-R27T and pGEMT-IFN-β-R27S as a template, the overlapping primer pair (iii) specific for GNITV and Pfu-turbo DNA polymerase under the same conditions, and the PCR product thus amplified was subjected to cloning as described above. As a result, the gene having the substitution of alanine at the $27^{th}$ position with threonine or serine and the addition of the codon encoding the amino acid sequence consisting of glycine-asparagine-isoleucine-threonine-valine was obtained. Plasmids containing such gene were designated pGEMT-IFN-β-R27T+GNITV and pGEMT-IFN-β-R27S+GNITV.

Table 1 shows the plasmids inserted with 5 interferon-beta mutein genes prepared according to the present invention, respectively.

gen) were treated with EcoRI and XhoI, respectively. The linearized IFN-β mutein gene and pcDNA3.1 were recovered from an agarose gel by using a Qiagen extraction kit, subjected to ligation, and then, transformed into E. coli DH5α. Plasmid DNA was purified from the colony generated after culturing the E. coli transformant in a LB-ampicillin agar medium, treated with restriction enzymes EcoRI and XhoI, and then, subjected to 1% agarose gel electrophoresis, to select the colony inserted with only the IFN-β mutein gene. It was confirmed that plasmid DNA of the selected colony has the nucleotide sequence of IFN-β mutein gene by sequencing analysis. Such plasmid was designated pcDNA3.1-IFN-β-X (wherein, X is a number of each interferon-beta mutein).

COS cells (ATCC No. CRL-1650) were transfected with the recombinant expression vectors corresponding to natural interferon-beta, interferon-beta muteins R27T, R27S, R27T+GNITV and R27S+GNITV among the prepared recombinant expression vectors, respectively. Namely, the pre-cultured COS cells were inoculated into a 60 mm tissue culture dish at a concentration of $2 \times 10^5$ cells/ml and incubated for 24 hrs. Each recombinant expression vector DNA 2 μg and 7 μl of a Lipofectin™ (Gibco BRL) reagent were added to 100 μl of DMEM having no serum, respectively, and kept at room temperature for 15 min. Two solutions thus prepared were mixed with each other and kept at room temperature for 15 min, to form a lipofectin-DNA complex. After a serum-free DMEM was added to the lipofectin-DNA complex, the mixture was gently placed on the COS cells cultured in the plate, and the plate was incubated in a 37° C., 5% $CO_2$ incubator for 6 hrs to occur the transfection. The COS cells transfected with each expression vector were cultured in DMEM supplemented with 10% fetal bovine serum (JRH), 50 μg/ml of penicillin and 50 μg/ml of streptomycin at 37° C., 5% $CO_2$ for 48 hrs. During the cultivation, the conditioned culture solution was collected for 3 to 5 days.

TABLE 1

Interferon-beta mutein genes

| Plasmid | Amino acid substitution | Substitution and addition |
|---|---|---|
| pGEMT-IFN-β-R27T | R27T | AGG→ACG |
| pGEMT-IFN-β-R27S | R27S | AGG→AGT |
| pGEMT-IFN-β-GNITV | GNITV | +GGTAATATC ACTGTC |
| pGEMT-IFN-β-R27T+GNITV | R27T+GNITV | AGG→ACG +GGTAATATC ACTGTC |
| pGEMT-IFN-β-R27S+GNITV | R27S+GNITV | AGG→AGT +GGTAATATC ACTGTC |

Example 2

Figure 3:
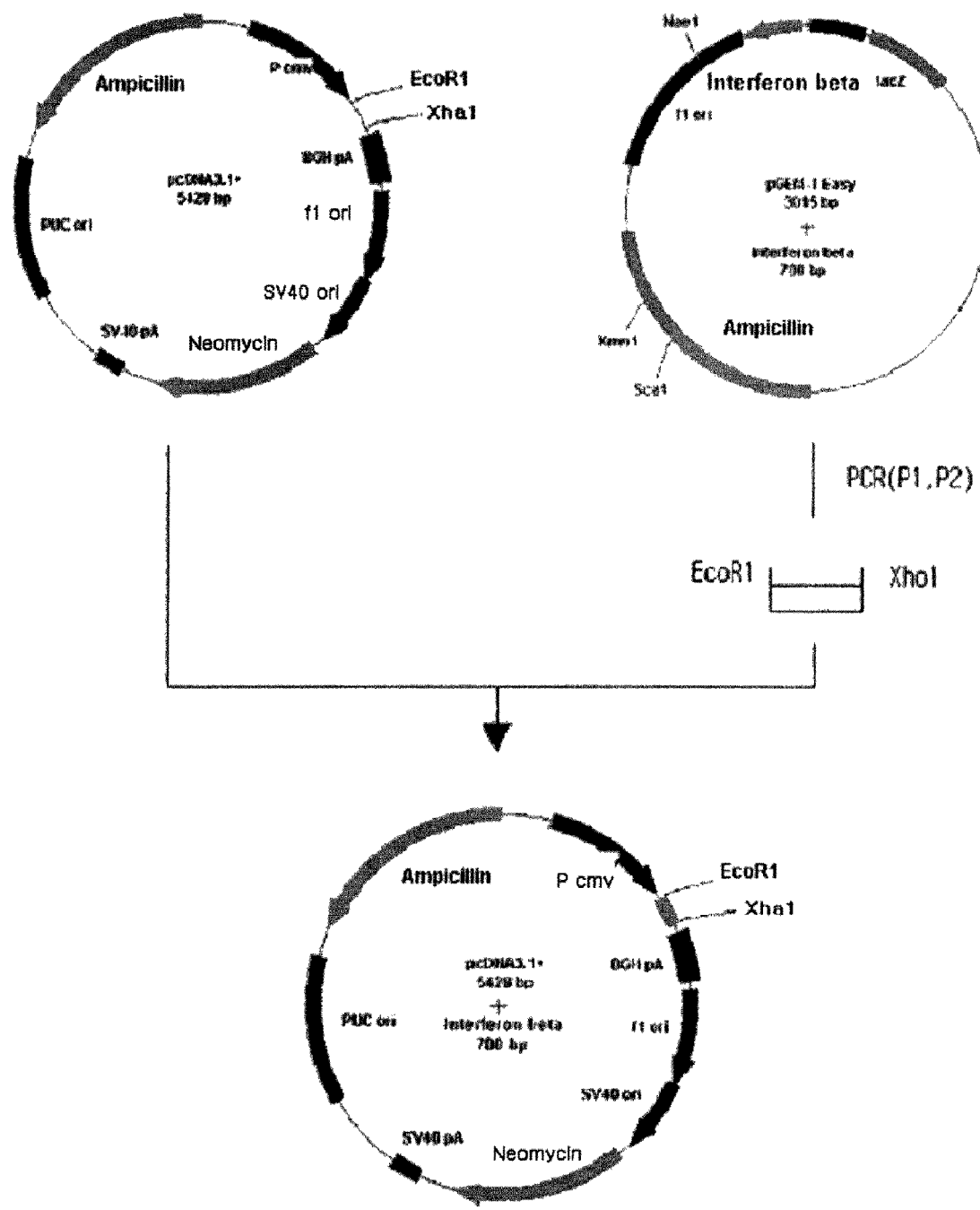
FIG. 3 is a scheme showing the procedure of assembling expression vector pcDNA3.1-IFN-β for the expression of a human interferon-beta mutein.

Construction of an Expression Vector, Transfection into COS Cells and Cell Culture PCR was carried out by using each of the plasmids containing the interferon-beta mutein prepared in Example 1 as a template and a primer pair of P1 (CCGGAATTCGCCACCATGACCAACAAGTGTCTCCTCCAAA, SEQ ID NO: 10) and P2 (CCGCTCGAGGTCACTTAAACAGCATCTGCTGGTTGA, SEQ ID NO: 11), to obtain the genes encoding artificially substituted interferon-beta (FIG. 3). At this time, DNA polymerase (Stratagene) was employed in this PCR reaction, and the amplified gene had recognition sites for restriction enzymes EcoRI and XhoI at its both ends. The IFN-β mutein gene thus amplified and pcDNA3.1 (Invitro- Example 3

Characterization of Interferon-Beta Mutein

Example 3-1

Confirmation of Sugar Chain Addition

The supernatant containing the recombinant human interferon-beta or the interferon-beta mutein was separated from the culture solution of the transfected COS cells prepared in Example 2. The supernatant 1~2 μg was mixed with an anti-interferon-beta rabbit polyclonal antibody and was subjected to immunoprecipitation at room temperature overnight. Protein A sepharose resin 20 to 80 μl diluted with PBS (phosphate buffered saline) at an equal volume was added to the supernatant containing the antibody, and the mixture was reacted at room temperature for an hour. The mixture was subjected to centrifugation to separate a pellet, and the pellet was washed with PBS. A part of the pellet was treated with N-glycanase to cut a N-linked sugar chain. The pellets treated with and without N-glycanase were subjected to 15% SDS-polyacrylamide gel electrophoresis. The gels were transferred onto a nitrocellulose membrane and subjected to western blot analysis using an anti-interferon-beta mouse monoclonal antibody according to the method described by Runkel et al (*Pharmaceutical Research* 15: 641-649, 1998).

Figure 5:
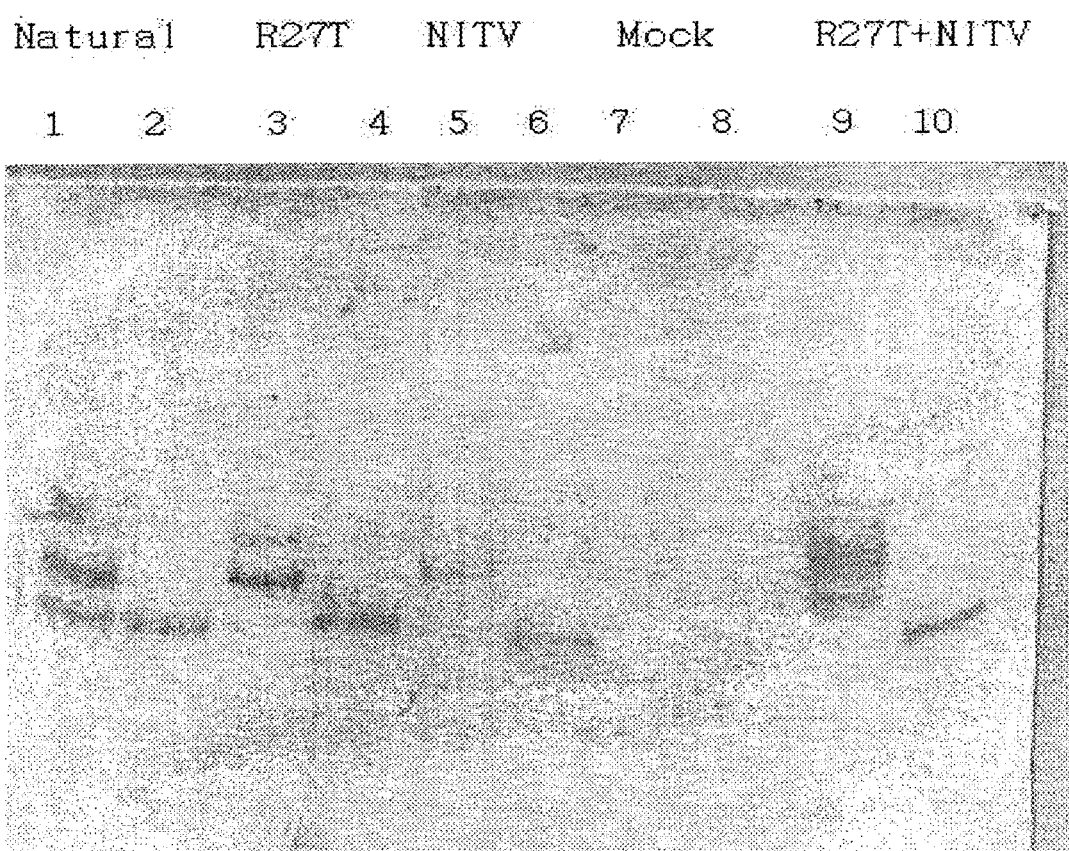
FIG. 5 shows the result of western blot analyzing the expression of interferon-beta muteins in COS cells. In addition, it shows also the result of western blot analyzing the muteins after the treatment with N-glycanase. A monoclonal antibody specific for human interferon-beta is used as a primary antibody and a HRP-conjugated anti-mouse immunoglobulin rabbit antibody is used as a secondary antibody.

As a result of analyzing the supernatant of the COS cells transfected with each of the interferon-beta muteins, it has been confirmed that its protein molecular weight of the interferon-beta mutein increases compared to that of the natural interferon-beta (FIG. 5). When the interferon-beta mutein having the increased protein molecular weight was treated with N-glycanase, its sugar chain was removed, which results in decreasing the molecular weight (FIG. 5).

Example 3-2

Activity Comparison of Interferon-Beta Muteins

To compare the activities of natural interferon-beta and interferon-beta muteins, the amount of the interferon protein was quantified via EIA (enzyme immunoassay), and titers of the natural interferon-beta and interferon-beta muteins were measured through a viral activity test.

EIA was performed by using a kit (PBL) according to the manufacturer's instruction. Namely, 100 µl of a diluting solution was distributed to each well specified within an antibody-absorbing plate included in the enzyme immunoassay kit. An international standard solution and samples were diluted with a diluting solution at a proper dilution rate and 100 µl each of the diluents were added to the well. The plate was kept at room temperature for an hour. At this time, the international standard solution was prepared by dissolving one ample of the human IFN-β international standard (NIBSC) in 1 µl of a formulation buffer and distributing 100 µl of the resulting solution to a vial. The vial was stored at −70° C., and when used, the frozen vial was melted and the content was properly diluted with a diluting solution before the use. After the residual reaction solution was removed from each well, the well plate was washed with 250 µl of a washing solution three times, and 100 µl of an enzyme-antibody conjugate solution was added to each well. The well plate was kept at room temperature for an hour. After the reaction was completed, the reaction solution was removed. The well plate was washed with 200 µl of a washing solution three times and the residual solution was completely removed therefrom. A pre-prepared substrate-coloring solution 100 µl was then added to each well and reacted at room temperature for 30 min. After the reaction was completed, 100 µl of a reaction stop solution was added to each well to stop the reaction and the absorbance was measured at 450 nm. A standard curve was drawn by plotting a concentration of the standard solution to a horizontal axis and the absorbance (A450 nm) thereof to a traverse axis, and the concentration of human IFN-β corresponding to each absorbance of the international standard solution and samples was calculated from the standard curve. The average value of three diluent concentrations was determined by multiplying the calculated concentration by each dilution rate, the measured values of the international standard solution and samples were calculated therefrom, and then, the final concentration was calculated. The antiviral activity test was performed according to the same method as described in Example 6. The ratio of antiviral titer and EIA value in the several culture solutions of COS cells transiently expressing each interferon-beta mutein are shown in Table 2. From these results, it has been confirmed that the molecular weight of the interferon-beta mutein increases due to the addition of sugar chain, and its activity also is equal to or higher than that of the natural interferon-beta. For the mass-production of such interferon-beta mutein, the interferon-beta mutein expression vector described above was transfected into CHO cell line.

TABLE 2

Increase in the molecular weight of the interferon-beta mutein and the ratio of antiviral titer and EIA value

| Mutein No. | Amino acid substitution | Increase in molecular weight | Ratio of antiviral titer and EIA value |
|---|---|---|---|
| R27T | R27T | ++ | 3 |
| R27S | R27S | ++ | 3 |
| NITV | NITV | ++ | 1.5 |
| R27T+GNITV | R27T+GNITV | ++++ | 4 |
| R27S+GNITV | R27S+GNITV | ++++ | 4 |

++: the molecular weight is 26 kDa which is added one sugar chain thereto.
++++: the molecular weight is 30 kDa which is added two sugar chains thereto.

Example 4

Transfection and Cell Culture (CHO Cells)

Figure 4:
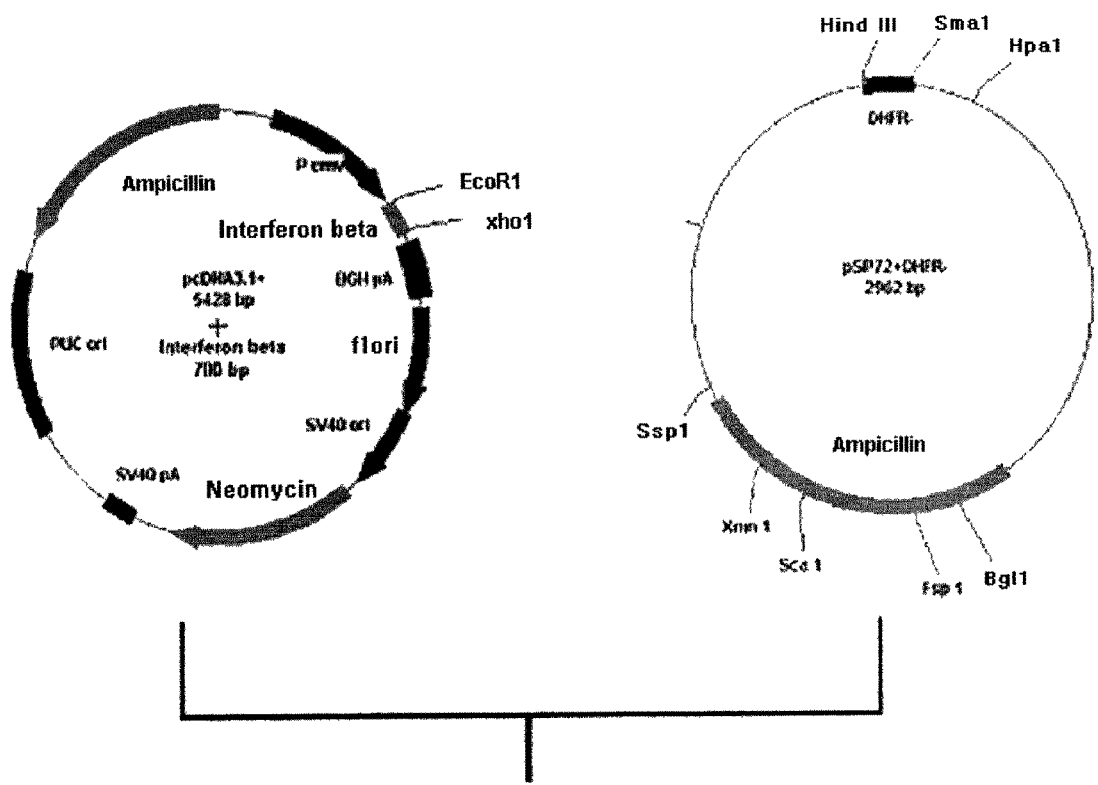
FIG. 4 is a scheme showing the procedure of co-transfecting expression vector pcDNA3.1-IFN-β and psp72-DHFR into an animal cell for the expression of a human interferon-beta mutein.

CHO cells (DG44) were grown in a 60 mm cell culture dish until their confluence reaches to about 40~80% ($1~4×10^5$ cells/60 mm dish). A Lipofectin™ reagent 3 µl (Gibco) was well mixed with 97 µl of α-MEM (serum-free and antibiotics-free), and plasmid pcDNA3.1-IFN-β-X DNA (0.1 µg/µl or more, about 2 µg) and pSP72-DHFR (0.2 µg) were added thereto. After the mixture was kept at room temperature for 30 min, it added to the CHO cells cultured above (FIG. 4). One day after, the culture medium was replaced with alpha-MEM supplemented with 50 µg/ml of G418 and 10% FBS. Subsequently, the cells were cultured in alpha-MEM minimal medium lacking deoxyribonucleoside and ribonucleoside for 7~10 days, to select transfectant cells. After then, CHO DHFR+ transfectant cells were secondarily selected. The secondarily selected CHO DHFR+ transfectant cells were subjected to colonization on a 96-well plate through a limiting dilution method and continuously cultured in a selective medium. Finally, the transfectant cells were cultured in a minimal medium containing 10% serum with gradually increasing MTX (methotrexate, Sigma) concentration by 2-fold from 20 nM to 1000 nM, to tertiarily select MTX resistant clones grown in the MTX selective medium.

A single cell was separated from the healthy cell line grown in the medium containing 1 µM of MTX for at least a month. First, after a single cell was inoculated into each well of a 96 well-multi plate and cultured, the well having only one single cell was selected. A candidate group showing a high expression rate was selected via EIA quantifying analysis. The selected candidate group was cultured by serially transferring it in a 24-well plate to a 6-well plate. The candidate group thus cultured was selected again via EIA quantifying analysis, to finally establish a high expression cell line of interferon-beta. As a result of measuring the amount of interferon-beta produced in the recombinant CHO cell line thus prepared above, while the natural interferon-beta cell line produced 1.8 µg/ml/24 hr of IFN-β, CHO-R27T and CHO-R27T-GNITV cell lines expressing the interferon-beta mutein produced 6.5

µg/ml/24 hr and 7.0 µg/ml/24 hr of IFN-β, respectively, which is 3-fold higher than that of the natural cell line.

Example 5

Purification of Interferon-Beta Added with One or More Sugar Chains Produced in CHO Cell Line The cell line incorporated with one or more mutein sequences in Example 4 was cultured by using a cell factory (Nunc, Cat No. 170069). Each expression cell line was diluted with alpha-MEM containing 10% FBS into a concentration of $5 \times 10^4$ cells/ml, and subcultured in the cell factory at 5% $CO_2$, 37° C. for 72 hrs, to confirm a cell growth. The cells were washed with PBS three times to remove the residual serum component at most, and its culture medium was replaced with a serum-free medium (Sigma C8730). After the replacement with the serum-free medium, the culture solution was collected at every 24 hrs four times and the fresh serum-free medium was added thereto each time for the collection. The total four collected culture solutions were subjected to purification. Blue sepharose resin (Amersham-Pharmacia) 200 ml was filled in XK50/20 column (Amersham-Pharmacia) and equilibrated with 10 C.V. (column volume) of a buffer A (20 mM sodium phosphate, 1 M NaCl, pH 7.4). The micro-filtered culture solution was flowed into the equilibrated column at a flow rate of 20 ml/min, and monitored by a UV detector at a wavelength of 280 nm. A buffer B (20 mM sodium phosphate, 1 M NaCl, 30% ethylene glycol, pH 7.4) was flowed into the column to remove unabsorbent components, and the protein absorbed to the resin was eluted with a buffer C (20 mM sodium phosphate, 1 M NaCl, 60% ethylen glycol, pH 7.4). The effluent was subjected to dialysis with PBS (phosphate buffered saline), concentrated with a concentrator (Centricon, Cut off 10,000), and then, subjected to dialysis again with PBS.

Example 6

Physicochemical Characterization of Interferon-Beta Added with One or More Sugar Chains Produced in CHO Cell Line

Example 6-1

SDS-PAGE and Western Blot Analysis

Figure 6:
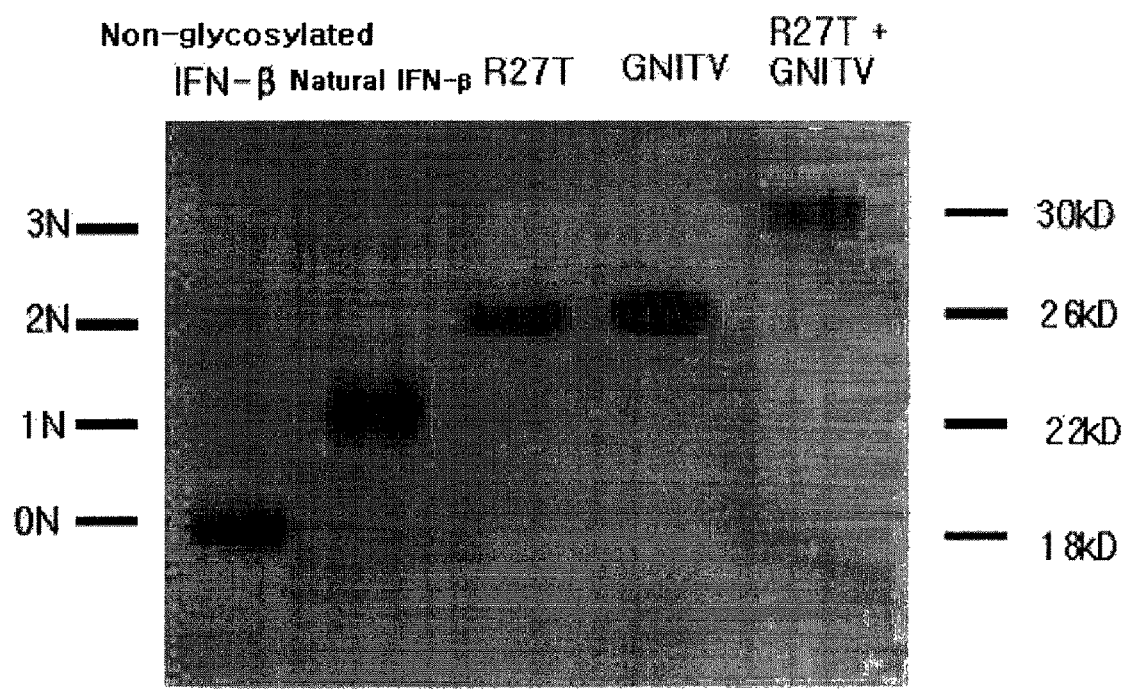
FIG. 6 shows the result of SDS-PAGE analyzing the interferon-beta muteins purified from a culture solution of CHO cells.

The sample purified in Example 5 was mixed with a 5× sample buffer (125 mM Tris-HCl, 5% SDS, 50% glycerol, 0.1% β-mercaptoethanol, 1 mg/ml bromophenol blue) at a ratio of 1:4, and the mixture was pre-treated at 95° C. for 5 min. The pre-treated mixture 20 µl was loaded onto a well of 15% polyacrylamide gel with a standard molecular weight marker and developed. After the electrophoresis was completed, the gel was stained with Coomassie brilliant blue and destained with a destaining solution. As a result, the natural interferon-beta showed about 18.0 kDa of a band corresponding to the protein having no sugar chain and about 22.0 kDa of a band corresponding to the protein having a sugar chain. In case of IFN-β introduced with one additional sugar chain, about 26.0 kDa of a band was additionally detected, and in case of IFN-β introduced with two additional sugar chains, about 30.0 kDa of a band was additionally detected, compared to the band pattern of the natural interferon-beta (FIG. 6).

Example 6-2

Test for Confirming the Addition of Sialic Acid to the Sugar Chain Terminal End The content of interferon-beta in all the purified proteins was measured by using a human IFN-β ELISA kit (PBL). The content of sialic acid in each protein was measured by modifying the method of Masaki Ito et al. (*Anal. Biochem.* 300: 260, 2002). Sialic acid was separated from a glycoprotein by reacting the purified protein with 0.1 N hydrochloric acid at 80° C. for an hour. Some of them was labeled with fluorescein by using a sialic acid fluorescence labeling kit (Takara) and subjected to HPLC to analyze the content. The results are shown in Table 3 as the % ratio of the weigh of sialic acid in the interferon-beta mutein compared to that of the natural interferon-beta.

TABLE 3

The weight of sialic acid in the interferon-beta mutein

| Interferon-beta | Weight of sialic acid/weight of IFN-β |
|---|---|
| Natural | 1.96 ± 0.14 |
| R27T, R27S | 3.50 ± 0.12 |
| GNITV | 3.23 ± 0.32 |
| R27T+GNITV, R27S+GNITV | 6.90 ± 0.25 |

Example 7

Biological Activity of Interferon-Beta Mutein Expressed in CHO Cells

Example 7-1

Antiviral Activities of R27T, R27S and GNITV Interferon-Beta Muteins

Antiviral activities of R27T, R27T+GNITV, GNITV interferon-beta muteins and the interferon-beta being removed its sugar chain (IFNβ-1b) were relatively compared each other based on the antiviral activity of the natural interferon-beta (IFNβ-1a). At this time, Rebif (Serono) was employed as the natural interferon-beta.

A549 cells were cultured in MEM supplemented with 10% FBS, 100×MEM unessential amino acid solution and 100 mM sodium pyruvate. At the day of such analysis, the cells were transferred to the same fresh medium and their cell density was adjusted to $3 \times 10^5$ cells/ml. Test and control interferon-betas were diluted with the same medium. Such dilution was carried out within a 96-well multiplate to be contained in the well at a volume of 100 µl/well and the samples were serially diluted by 2-told. All samples were prepared in two sets. Control wells containing only 100 µl of the medium (having no interferon-beta) were included therein. After 100 µl of the cells were added to each well, the well plate was incubated at 37° C., 5% $CO_2$ for 20 hrs. The medium was removed from the plate and 100 µl of EMCV (1000 $TCID_{50}$/ml) diluted with the same medium was added to each well. After the plate was incubated at 37° C., 5% $CO_2$ for 22 hrs, the medium was removed therefrom, and the plate was stained with crystal violet. After removing the dye, 100 µl of 2-methoxyethanol was added thereto to extract the dye, and the absorbance was measured at 450 µm to determine the antiviral activity.

Figure 7:
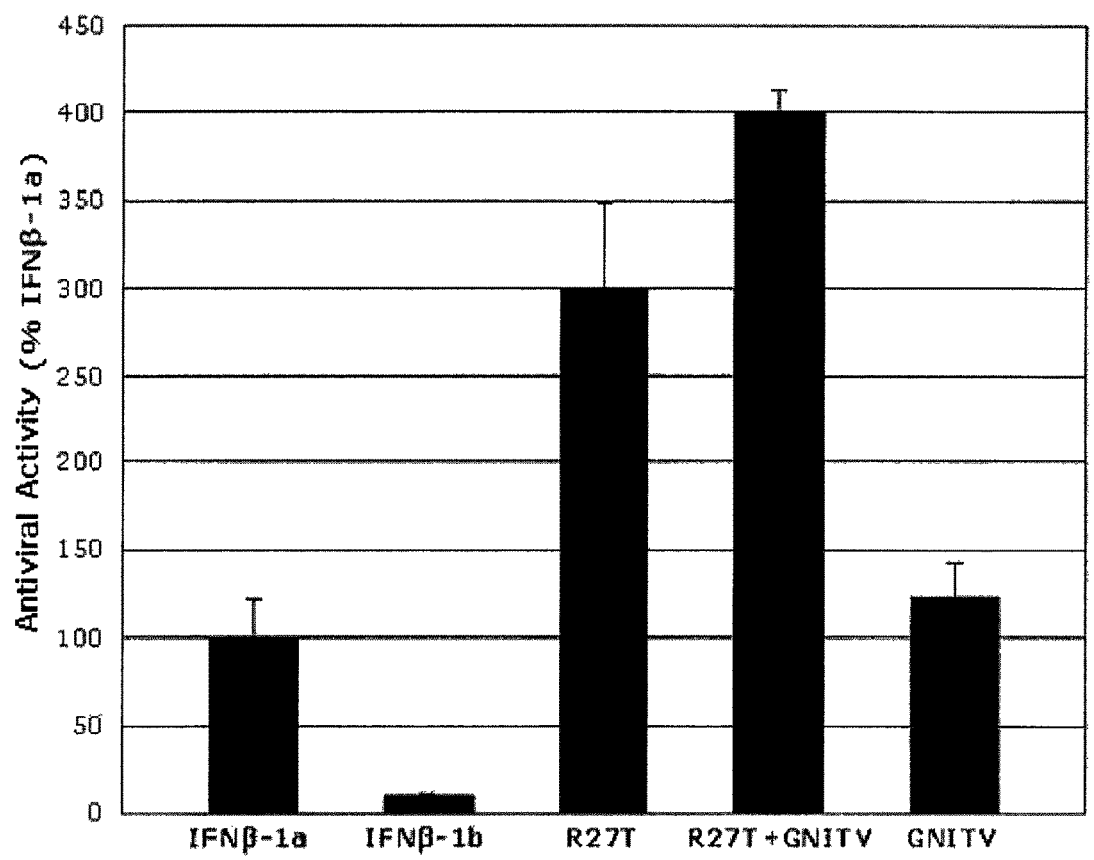
FIG. 7 shows the result of comparing the antiviral activities of the interferon-beta muteins expressed in CHO cells to that of natural interferon-beta.

While the interferon-beta being removed its sugar chain (IFNβ-1b) showed relatively low activity under the same condition, R27T, R27T+GNITV and GNITV showed higher activities than the natural interferon-beta (IFNβ-1a; Rebif). R27T+GNITV introduced with two additional sugar chains showed 4-fold higher activity than the natural interferon-beta, and R27T introduced with one additional sugar chain showed 3-fold higher activity than the same (FIG. 7).

Example 7-2

Inhibition of Cell Growth

Further the effects of interferon-beta muteins on cell growth were examined, and relatively compared each other based on the effect of the natural interferon-beta (IFNβ-1a) equal to the antiviral activity. At this time, Rebif (Serono) was employed as the natural interferon-beta. Anti-proliferation activity was measured by using Daudi cells.

Daudi cells were cultured in RPMI 1640 supplemented with 100 U/ml of penicillin, 100 mg/ml of streptomycin, 2 mM glutamine and 10% FBS. Test and control interferon-betas were serially diluted by 2-fold with RPMI 1640 containing 10% FBS within a 96-well multiplate to be contained in the well at a volume of 100 µl/well. All samples were prepared in two sets. The cells were added to a 96-well multiplate at a concentration of $1 \times 10^4$ cells/well, and the well plate was incubated at 37° C., 5% $CO_2$ for 40 to 48 hrs. Subsequently, 50 µl of the medium containing 1 µCi of $^3[H]$ thymidine was added to each well, and the well plate was incubated for 6 hrs. The cells were harvested and their incorporated amount of radioactivity was measured.

Figure 8:
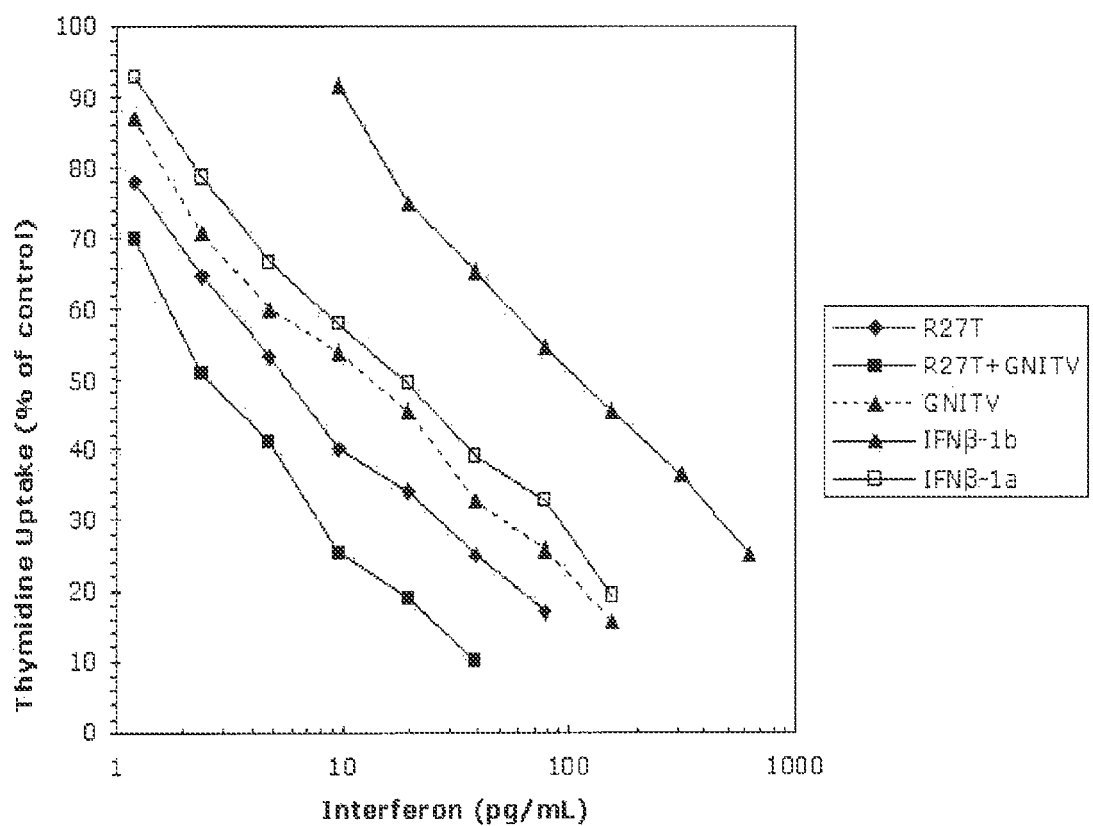
FIG. 8 shows the result of comparing the inhibitory effect on cell growth of the interferon-beta muteins expressed in CHO cells to that of natural interferon-beta.

The interferon-beta muteins suppressed the growth of Daudi cells and their activities were dose-dependent. The interferon-beta being removed its sugar chain (IFNβ-1b) showed lower anti-proliferation activity than the natural interferon-beta (IFNβ-1a), while R27T, R27T+GNITV and GNITV interferon-beta muteins showed higher activity than the same. The activities of the interferon-beta muteins were ranked in order of R27T+GNITV, R27T and GNITV (FIG. 8).

Example 7-3

Immunoregulatory Ability

Immunoregulatory abilities of the natural interferon-beta and muteins thereof were measured through the activation of MHC class I in A549 cells.

A549 cells were cultured in DMEM supplemented with 10% FBS and 2 mM glutamine. The cells were inoculated into the medium containing the 2-fold serially diluted natural interferon-beta, muteins thereof or interferon-beta being removed its sugar chain (IFNβ-1b) at a density of $1 \times 10^5$ cells/ml, respectively, and incubated at 37° C., 5% $CO_2$ for 48 hrs. The cells were treated with a Hank's buffered salt solution containing 5 mM EDTA and harvested by centrifugation. The pellet thus separated was suspended in a FACS buffer at a density of $2 \times 10^7$ cells/ml, and its expression amount of MHC class I was measured by FACS analysis. An anti-HLA ABC antibody coupled with biotin and streptavidin coupled with fluorescein were employed in this measurement, and all samples were made in two sets.

Figure 9:
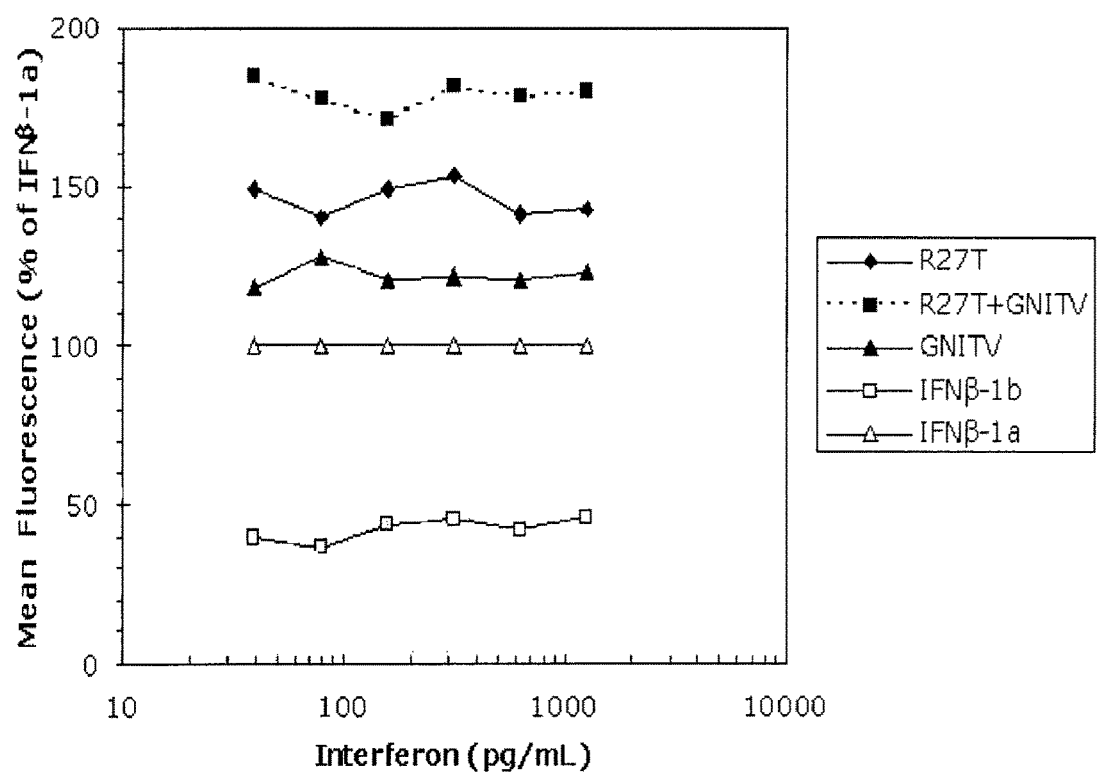
FIG. 9 shows the result of measuring the immunoregulatory effects of the interferon-beta muteins expressed in CHO cells and natural interferon-beta through the activation of MHC class I in A549 cells and comparing them.

The immunity enhancement effects of the interferon-beta muteins were similar to or slightly higher than that of the natural interferon-beta (IFNβ-1a). Such effects of the interferon-beta muteins were increased in order of GNITV, R27T and R27T+GNITV, which is equal to the above described two different activities. The interferon-beta having no additional sugar chain showed low immunoregulatory effect compared to its concentration (FIG. 9).

Example 7-4

Pharmacokinetic Constant Study

In vivo activity test was conducted according to the method which measures the change in blood concentration of the interferon-beta mutein depending on time in the rat administered with the interferon-beta mutein which was expressed in CHO cells. Hsd:Sprague-Dawley female rats having an average body weight of 246.3±258.1 g were employed in such in vivo activity test, and they were acclimated for a week to the cage environment being set temperature to 24±1° C., relative humidity to 55% and a lighting condition to 12 hrs light/12 hrs dark. The rats were bred in the same cage during the experiment.

After weighing the rats and making them randomly distributed according to their average body weights, they were divided into four groups of administering with the natural interferon-beta, two muteins and no drug, respectively, each consisting of 4 rats. Catheter was inserted at the jugular vein of the rats by a surgical operation 2 days before the experiment. The average body weight of the catheter inserted rats was 253.5 g.

Figure 10:
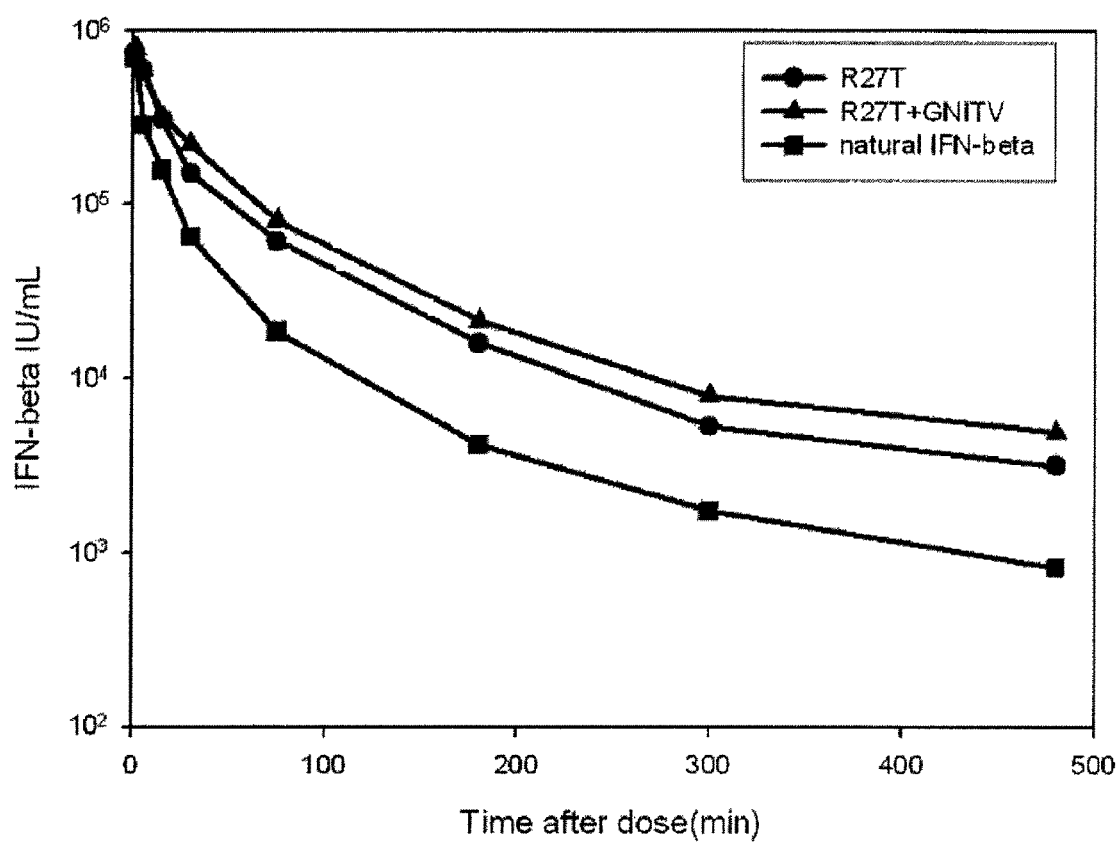
FIG. 10 shows the residual blood concentrations of the interferon-beta muteins expressed in CHO cells and natural interferon-beta in rats according to time-course.

The natural interferon-beta and each interferon-beta mutein were injected to the rats via tail vein as a test sample. The jugular vein catheter was washed with saline before the blood collection, and 0.3 ml of blood was collected at the time point corresponding to 1, 5, 15, 30, 75, 180, 300 and 480 min after the injection. After the blood collection, the catheter was filled with heparin saline (50 IU/ml) to prevent it from clogging. The collected blood samples were immediately treated with a 4% sodium citrate solution as an anticoagulant to prevent from coagulation, and subjected to centrifugation to separate the plasma except for hemocytes. The separated plasma was stored at −70° C. The blood concentration of the interferon-beta in the experimental animal was measured by an antiviral test. FIG. 10 shows the blood concentrations of the interferon-beta mutein and the natural interferon-beta remaining in the rats according to time-course. Further, pharmacokinetic constants were calculated from these residual blood concentrations.

The results are shown in Table 4. R27T+GNITV and R27S+GNITV interferon-beta muteins introduced with two additional sugar chains showed 3-fold prolonged half-life rather than that of the natural interferon-beta, and R27T, R27S and GNITV interferon-beta muteins introduced with one additional sugar chain showed 3-fold prolonged half-life rather than that of the natural interferon-beta.

TABLE 4

Half-lives of interferon-beta muteins and natural interferon-beta in rats

| Sample | AUC (hr*IU/ml) | Average retention time (hr) | Vss (ml/kg) | Clearance rate (ml/kg/hr) | Half-life (hr) |
|---|---|---|---|---|---|
| R27T | 203966 | 0.726214 | 65.0 | 100.1 | 2.48 |
| GNITV | 190610 | 0.647452 | 74.4 | 114.9 | 2.46 |
| R27T + GNITV | 316807 | 0.952376 | 45.1 | 60.5 | 3.50 |
| Natural | 116807 | 0.512376 | 96.1 | 187.5 | 1.13 |

As described above, according to the present invention, the interferon-beta muteins having improved or increased activity or ability compared to the natural interferon-beta can be provided.

Since the human interferon-beta muteins of the present invention further contain one or two additional sugar chains compared to the natural human interferon-beta, they show improved or increased antiviral activity, cell growth inhibitory activity, immunoregulatory ability, and prolonged half-life. This means that it is capable of reducing a dose and the number of injection times of human interferon-beta.

Meanwhile, according to the present invention, a gene encoding the interferon-beta mutein, an animal cell expression vector containing the gene, an animal cell transfected with the expression vector, a method for preparing the human interferon-beta mutein by culturing the animal cell and a pharmaceutical composition comprising the human interferon-beta are also provided.

While the invention has been described with respect to the above specific embodiments, it should be recognized that various modifications and changes may be made to the invention by those skilled in the art which also fall within the scope of the invention as defined by the appended claims.

What is claimed is:

1. An isolated N-glycosylated polypeptide, wherein the polypeptide has the amino acid sequence selected from the group consisting of SEQ ID NOs: 18, 19 and 20.

2. The polypeptide of claim 1, wherein the polypeptide has the amino acid sequence of SEQ ID NO:18, consisting of:
   a human interferon-beta, represented by SEQ ID NO:1;
   a glycine-asparagine-isoleucine-threonine-valine (GNITV) sequence, which is represented by SEQ ID NO: 12; and
   two N-linked sugar chains,
   wherein, the GNITV sequence is attached at C-terminal end of SEQ ID NO:1 and the two N-linked sugar chains are on asparagines on amino acid positions $80^{th}$ and $168^{th}$ of SEQ ID NO:18.

3. The polypeptide of claim 1, wherein the polypeptide has the amino acid sequence of SEQ ID NO:19, consisting of:
   a human interferon-beta, represented by SEQ ID NO:1; and
   two N-linked sugar chains,
   wherein, the amino acid residue on the $27^{th}$ amino acid position of SEQ ID NO:1 is serine or threonine as represented by SEQ ID NO:2; and the two N-linked sugar chains are on asparagines on amino acid positions $25^{th}$ and $80^{th}$ of SEQ ID NO:19.

4. The polypeptide of claim 1, wherein the polypeptide has the amino acid sequence of SEQ ID NO:20, consisting of:
   a human interferon-beta, represented by SEQ ID NO:1;
   a glycine-asparagine-isoleucine-threonine-valine (GNITV) sequence, which is represented by SEQ ID NO: 12; and
   three N-linked sugar chains,
   wherein, the amino acid residue on the $27^{th}$ amino acid position of SEQ ID NO:1 is serine or threonine as represented by SEQ ID NO:2; the GNITV sequence is attached at C-terminal end of SEQ ID NO:2 and the three N-linked sugar chains are on asparagines on amino acid positions $25^{th}$, $80^{th}$ and $168^{th}$ of SEQ ID NO:20.

5. An isolated expression vector expressing the polypeptide of claim 1.

6. An isolated animal cell transfected with the expression vector of claim 5.

7. An isolated polynucleotide encoding the polypeptide of claim 1.

8. A method for preparing a polypeptide comprising,
   culturing an animal cell transfected with an expression vector containing the polynucleotide of claim 7.

9. A pharmaceutical composition comprising any one of the polypeptide of claim 1.

10. The pharmaceutical composition of claim 9, which shows an equivalent or improved pharmacological effect of natural human interferon-beta.

11. The pharmaceutical composition of claim 10, wherein the pharmacological effect is treating cancer, auto-immune disorder, or viral infection.

12. The pharmaceutical composition of claim 10, wherein the pharmacological effect is treating Hepatitis C.

13. The pharmaceutical composition of claim 10, wherein the pharmacological effect is treating multiple sclerosis.

* * * * *

SEQUENCE LISTING

```
<160> NUMBER OF SEQ ID NOS: 22

<210> SEQ ID NO 1
<211> LENGTH: 166
<212> TYPE: PRT
<213> ORGANISM: Homo sapiens
<220> FEATURE:
<223> OTHER INFORMATION: non-glycosylated human IFN-beta

<400> SEQUENCE: 1

Met Ser Tyr Asn Leu Leu Gly Phe Leu Gln Arg Ser Ser Asn Phe Gln
  1               5                  10                  15

Cys Gln Lys Leu Leu Trp Gln Leu Asn Gly Arg Leu Glu Tyr Cys Leu
             20                  25                  30

Lys Asp Arg Met Asn Phe Asp Ile Pro Glu Glu Ile Lys Gln Leu Gln
         35                  40                  45

Gln Phe Gln Lys Glu Asp Ala Ala Leu Thr Ile Tyr Glu Met Leu Gln
     50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 2
<211> LENGTH: 166
<212> TYPE: PRT
<213> ORGANISM: Artificial Sequence
<220> FEATURE:
<223> OTHER INFORMATION: R27T/S: non-glycosylated human IFN-beta
<220> FEATURE:
<221> NAME/KEY: VARIANT
<222> LOCATION: (27)
<223> OTHER INFORMATION: Xaa is Ser or Thr

<400> SEQUENCE: 2

Met Ser Tyr Asn Leu Leu Gly Phe Leu Gln Arg Ser Ser Asn Phe Gln
  1               5                  10                  15
```

```
Cys Gln Lys Leu Leu Trp Gln Leu Asn Gly Xaa Leu Glu Tyr Cys Leu
             20                  25                  30

Lys Asp Arg Met Asn Phe Asp Ile Pro Glu Glu Ile Lys Gln Leu Gln
         35                  40                  45

Gln Phe Gln Lys Glu Asp Ala Ala Leu Thr Ile Tyr Glu Met Leu Gln
     50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 3
<211> LENGTH: 498
<212> TYPE: DNA
<213> ORGANISM: Homo sapiens
<220> FEATURE:
<223> OTHER INFORMATION: gene encoding natural human IFN-beta

<400> SEQUENCE: 3
atgagctaca acttgcttgg attcctacaa agaagcagca attttcagtg tcagaagctc      60
ctgtggcaat tgaatgggag gcttgaatat tgcctcaagg acaggatgaa ctttgacatc     120
cctgaggaga ttaagcagct gcagcagttc cagaaggagg acgccgcatt gaccatctat     180
gagatgctcc agaacatctt tgctattttc agacaagatt catctagcac tggctggaat     240
gagactattg ttgagaacct cctggctaat gtctatcatc agataaacca tctgaagaca     300
gtcctggaag aaaaactgga gaaagaagat tttaccaggg gaaaactcat gagcagtctg     360
cacctgaaaa gatattatgg gaggattctg cattacctga aggccaagga gtacagtcac     420
tgtgcctgga ccatagtcag agtggaaatc ctaaggaact tttacttcat taacagactt     480
acaggttacc tccgaaac                                                   498

<210> SEQ ID NO 4
<211> LENGTH: 31
<212> TYPE: DNA
<213> ORGANISM: Artificial Sequence
<220> FEATURE:
<223> OTHER INFORMATION: forward primer for R27T:
      non-glycosylated human IFN-beta Thr at 27

<400> SEQUENCE: 4
gcaattgaat gggacgcttg aatactgcct c                                     31

<210> SEQ ID NO 5
<211> LENGTH: 31
<212> TYPE: DNA
<213> ORGANISM: Artificial Sequence
<220> FEATURE:
<223> OTHER INFORMATION: reverse primer for R27T:
      non-glycosylated human IFN-beta Thr at 27
```

-continued

```
<400> SEQUENCE: 5
gaggcagtat tcaagcgtcc cattcaattg c                                  31

<210> SEQ ID NO 6
<211> LENGTH: 31
<212> TYPE: DNA
<213> ORGANISM: Artificial Sequence
<220> FEATURE:
<223> OTHER INFORMATION: forward primer for R27S:
      non-glycosylated human IFN-beta Ser at 27

<400> SEQUENCE: 6
gcaattgaat gggagtcttg aatactgcct c                                  31

<210> SEQ ID NO 7
<211> LENGTH: 31
<212> TYPE: DNA
<213> ORGANISM: Artificial Sequence
<220> FEATURE:
<223> OTHER INFORMATION: reverse primer for R27S:
      non-glycosylated human IFN-beta Ser at 27

<400> SEQUENCE: 7
gaggcagtat tcaagactcc cattcaattg c                                  31

<210> SEQ ID NO 8
<211> LENGTH: 57
<212> TYPE: DNA
<213> ORGANISM: Artificial Sequence
<220> FEATURE:
<223> OTHER INFORMATION: forward primer for GNITV synthetic peptide

<400> SEQUENCE: 8
cttacaggtt acctccgaaa cggtaatatc actgtctgaa gatctcctag cctgtcc      57

<210> SEQ ID NO 9
<211> LENGTH: 57
<212> TYPE: DNA
<213> ORGANISM: Artificial Sequence
<220> FEATURE:
<223> OTHER INFORMATION: reverse primer for GNITV synthetic peptide

<400> SEQUENCE: 9
gaatgtccaa tggaggcttt gccattatag tgacagactt ctagaggatc ggacagg      57

<210> SEQ ID NO 10
<211> LENGTH: 40
<212> TYPE: DNA
<213> ORGANISM: Artificial Sequence
<220> FEATURE:
<223> OTHER INFORMATION: P1 primer for substituted Human IFN-beta

<400> SEQUENCE: 10
ccggaattcg ccaccatgac caacaagtgt ctcctccaaa                         40

<210> SEQ ID NO 11
<211> LENGTH: 36
<212> TYPE: DNA
<213> ORGANISM: Artificial Sequence
<220> FEATURE:
<223> OTHER INFORMATION: P2 primer for substituted Human IFN-beta

<400> SEQUENCE: 11
ccgctcgagg tcacttaaac agcatctgct ggttga                             36

<210> SEQ ID NO 12
```

-continued

```
<211> LENGTH: 5
<212> TYPE: PRT
<213> ORGANISM: Artificial Sequence
<220> FEATURE:
<223> OTHER INFORMATION: GNITV: synthetic peptide

<400> SEQUENCE: 12

Gly Asn Ile Thr Val
 1               5

<210> SEQ ID NO 13
<211> LENGTH: 171
<212> TYPE: PRT
<213> ORGANISM: Artificial Sequence
<220> FEATURE:
<223> OTHER INFORMATION: sequence 1-GNITV: Human IFN-beta-GNITV

<400> SEQUENCE: 13

Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Leu Glu Tyr Cys Leu
             20                  25                  30

Lys Asp Arg Met Asn Phe Asp Ile Pro Glu Glu Ile Lys Gln Leu Gln
         35                  40                  45

Gln Phe Gln Lys Glu Asp Ala Ala Leu Thr Ile Tyr Glu Met Leu Gln
     50                  55                  60

Asn Ile Phe Ala Ile Phe Arg Gln Asp Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn Gly Asn Ile Thr Val
                165                 170

<210> SEQ ID NO 14
<211> LENGTH: 171
<212> TYPE: PRT
<213> ORGANISM: Artificial Sequence
<220> FEATURE:
<223> OTHER INFORMATION: sequence 2-GNITV: Human IFN-beta-T/S at
      27-GNITV
<220> FEATURE:
<221> NAME/KEY: VARIANT
<222> LOCATION: (27)
<223> OTHER INFORMATION: Xaa is Ser or Thr

<400> SEQUENCE: 14

Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Xaa Leu Glu Tyr Cys Leu
             20                  25                  30

Lys Asp Arg Met Asn Phe Asp Ile Pro Glu Glu Ile Lys Gln Leu Gln
         35                  40                  45

Gln Phe Gln Lys Glu Asp Ala Ala Leu Thr Ile Tyr Glu Met Leu Gln
     50                  55                  60
```

```
Asn Ile Phe Ala Ile Phe Arg Gln Asp Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn Gly Asn Ile Thr Val
                165                 170

<210> SEQ ID NO 15
<211> LENGTH: 166
<212> TYPE: PRT
<213> ORGANISM: Artificial Sequence
<220> FEATURE:
<223> OTHER INFORMATION: R27S: Human IFN-beta Ser at 27

<400> SEQUENCE: 15

Met Ser Tyr Asn Leu Leu Gly Phe Leu Gln Arg Ser Ser Asn Phe Gln
  1               5                  10                  15

Cys Gln Lys Leu Leu Trp Gln Leu Asn Gly Ser Leu Glu Tyr Cys Leu
                 20                  25                  30

Lys Asp Arg Met Asn Phe Asp Ile Pro Glu Glu Ile Lys Gln Leu Gln
             35                  40                  45

Gln Phe Gln Lys Glu Asp Ala Ala Leu Thr Ile Tyr Glu Met Leu Gln
     50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 16
<211> LENGTH: 166
<212> TYPE: PRT
<213> ORGANISM: Artificial Sequence
<220> FEATURE:
<223> OTHER INFORMATION: R27T: Human IFN-beta Thr at 27

<400> SEQUENCE: 16

Met Ser Tyr Asn Leu Leu Gly Phe Leu Gln Arg Ser Ser Asn Phe Gln
  1               5                  10                  15

Cys Gln Lys Leu Leu Trp Gln Leu Asn Gly Thr Leu Glu Tyr Cys Leu
                 20                  25                  30
```

```
Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 17
<211> LENGTH: 166
<212> TYPE: PRT
<213> ORGANISM: Homo sapiens
<220> FEATURE:
<223> OTHER INFORMATION: N-glycosylated human IFN-beta
<220> FEATURE:
<221> NAME/KEY: VARIANT
<222> LOCATION: (80)
<223> OTHER INFORMATION: Xaa is N-glycosylated Asn

<400> SEQUENCE: 17

Met Ser Tyr Asn Leu Leu Gly Phe Leu Gln Arg Ser Ser Asn Phe Gln
  1               5                  10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60

Asn Ile Phe Ala Ile Phe Arg Gln Asp Ser Ser Ser Thr Gly Trp Xaa
 65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 18
<211> LENGTH: 171
<212> TYPE: PRT
<213> ORGANISM: Artificial Sequence
```

```
<220> FEATURE:
<223> OTHER INFORMATION: Glycosylated human IFN-beta-GNITV
<220> FEATURE:
<221> NAME/KEY: VARIANT
<222> LOCATION: (80)
<223> OTHER INFORMATION: Xaa is N-glycosylated Asn
<220> FEATURE:
<221> NAME/KEY: VARIANT
<222> LOCATION: (168)
<223> OTHER INFORMATION: Xaa is N-glycosylated Asn

<400> SEQUENCE: 18

Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60

Asn Ile Phe Ala Ile Phe Arg Gln Asp Ser Ser Ser Thr Gly Trp Xaa
 65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn Gly Xaa Ile Thr Val
                165                 170

<210> SEQ ID NO 19
<211> LENGTH: 166
<212> TYPE: PRT
<213> ORGANISM: Artificial Sequence
<220> FEATURE:
<223> OTHER INFORMATION: Glycosylated human IFN-beta T/S at 27
<220> FEATURE:
<221> NAME/KEY: VARIANT
<222> LOCATION: (25)
<223> OTHER INFORMATION: Xaa is N-glycosylated Asn
<220> FEATURE:
<221> NAME/KEY: VARIANT
<222> LOCATION: (27)
<223> OTHER INFORMATION: Xaa is Ser or Thr
<220> FEATURE:
<221> NAME/KEY: VARIANT
<222> LOCATION: (80)
<223> OTHER INFORMATION: Xaa is N-glycosylated Asn

<400> SEQUENCE: 19

Met Ser Tyr Asn Leu Leu Gly Phe Leu Gln Arg Ser Ser Asn Phe Gln
 1               5                  10                  15

Cys Gln Lys Leu Leu Trp Gln Leu Xaa Gly Xaa Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60
```

```
Asn Ile Phe Ala Ile Phe Arg Gln Asp Ser Ser Ser Thr Gly Trp Xaa
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```

<210> SEQ ID NO 20
<211> LENGTH: 171
<212> TYPE: PRT
<213> ORGANISM: Artificial Sequence
<220> FEATURE:
<223> OTHER INFORMATION: Glycosylated human IFN-beta-T/S at 27-GNITV
<220> FEATURE:
<221> NAME/KEY: VARIANT
<222> LOCATION: (25)
<223> OTHER INFORMATION: Xaa is N-glycosylated Asn
<220> FEATURE:
<221> NAME/KEY: VARIANT
<222> LOCATION: (27)
<223> OTHER INFORMATION: Xaa is Ser or Thr
<220> FEATURE:
<221> NAME/KEY: VARIANT
<222> LOCATION: (80)
<223> OTHER INFORMATION: Xaa is N-glycosylated Asn
<220> FEATURE:
<221> NAME/KEY: VARIANT
<222> LOCATION: (168)
<223> OTHER INFORMATION: Xaa is N-glycosylated Asn

<400> SEQUENCE: 20

```
Met Ser Tyr Asn Leu Leu Gly Phe Leu Gln Arg Ser Ser Asn Phe Gln
  1               5                  10                  15

Cys Gln Lys Leu Leu Trp Gln Leu Xaa Gly Xaa Leu Glu Tyr Cys Leu
             20                  25                  30

Lys Asp Arg Met Asn Phe Asp Ile Pro Glu Glu Ile Lys Gln Leu Gln
         35                  40                  45

Gln Phe Gln Lys Glu Asp Ala Ala Leu Thr Ile Tyr Glu Met Leu Gln
     50                  55                  60

Asn Ile Phe Ala Ile Phe Arg Gln Asp Ser Ser Ser Thr Gly Trp Xaa
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn Gly Xaa Ile Thr Val
                165                 170
```

```
<210> SEQ ID NO 21
<211> LENGTH: 166
<212> TYPE: PRT
<213> ORGANISM: Artificial Sequence
<220> FEATURE:
<223> OTHER INFORMATION: Glycosylated human IFN-beta Ser at 27
<220> FEATURE:
<221> NAME/KEY: VARIANT
<222> LOCATION: (25)
<223> OTHER INFORMATION: Xaa is N-glycosylated Asn
<220> FEATURE:
<221> NAME/KEY: VARIANT
<222> LOCATION: (80)
<223> OTHER INFORMATION: Xaa is N-glycosylated Asn

<400> SEQUENCE: 21

Met Ser Tyr Asn Leu Leu Gly Phe Leu Gln Arg Ser Ser Asn Phe Gln
 1               5                  10                  15

Cys Gln Lys Leu Leu Trp Gln Leu Xaa Gly Ser Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
     50                  55                  60

Asn Ile Phe Ala Ile Phe Arg Gln Asp Ser Ser Ser Thr Gly Trp Xaa
 65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 22
<211> LENGTH: 166
<212> TYPE: PRT
<213> ORGANISM: Artificial Sequence
<220> FEATURE:
<223> OTHER INFORMATION: Glycosylated human IFN-beta Thr at 27
<220> FEATURE:
<221> NAME/KEY: VARIANT
<222> LOCATION: (25)
<223> OTHER INFORMATION: Xaa is N-glycosylated Asn
<220> FEATURE:
<221> NAME/KEY: VARIANT
<222> LOCATION: (80)
<223> OTHER INFORMATION: Xaa is N-glycosylated Asn

<400> SEQUENCE: 22

Met Ser Tyr Asn Leu Leu Gly Phe Leu Gln Arg Ser Ser Asn Phe Gln
 1               5                  10                  15

Cys Gln Lys Leu Leu Trp Gln Leu Xaa Gly Thr Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
     50                  55                  60
```

```
Asn Ile Phe Ala Ile Phe Arg Gln Asp Ser Ser Thr Gly Trp Xaa
 65              70              75              80

Glu Thr Ile Val Glu Asn Leu Leu Ala Asn Val Tyr His Gln Ile Asn
             85              90              95

His Leu Lys Thr Val Leu Glu Glu Lys Leu Glu Lys Glu Asp Phe Thr
            100             105             110

Arg Gly Lys Leu Met Ser Ser Leu His Leu Lys Arg Tyr Tyr Gly Arg
            115             120             125

Ile Leu His Tyr Leu Lys Ala Lys Glu Tyr Ser His Cys Ala Trp Thr
            130             135             140

Ile Val Arg Val Glu Ile Leu Arg Asn Phe Tyr Phe Ile Asn Arg Leu
145             150             155             160

Thr Gly Tyr Leu Arg Asn
            165
```